(12) United States Patent
Zhang et al.

(10) Patent No.: US 9,782,089 B2
(45) Date of Patent: Oct. 10, 2017

(54) WORKSHEET SYSTEM FOR DETERMINING MEASURED PATIENT VALUES FOR USE IN CLINICAL ASSESSMENT AND CALCULATIONS

(75) Inventors: Hongxuan Zhang, Palatine, IL (US); Harold James Wade, Rockford, IL (US); Gene Moy, Elgin, IL (US); Anthony Lawrence, Hoffman Estates, IL (US)

(73) Assignee: Siemens Healthcare GmbH (DE)

( * ) Notice: Subject to any disclaimer, the term of this patent is extended or adjusted under 35 U.S.C. 154(b) by 1251 days.

(21) Appl. No.: 13/108,064

(22) Filed: May 16, 2011

(65) Prior Publication Data

US 2012/0059269 A1    Mar. 8, 2012

Related U.S. Application Data

(60) Provisional application No. 61/380,757, filed on Sep. 8, 2010.

(51) Int. Cl.
| | | |
|---|---|---|
| *A61B 5/026* | (2006.01) | |
| *A61B 5/029* | (2006.01) | |
| *G06F 19/00* | (2011.01) | |
| *A61B 5/0205* | (2006.01) | |
| *A61B 5/021* | (2006.01) | |
| *A61B 5/0215* | (2006.01) | |
| *A61B 5/08* | (2006.01) | |
| *A61B 5/1455* | (2006.01) | |

(52) U.S. Cl.
CPC ............. *A61B 5/026* (2013.01); *A61B 5/029* (2013.01); *G06F 19/345* (2013.01); *G06F 19/3487* (2013.01); *A61B 5/021* (2013.01); *A61B 5/0205* (2013.01); *A61B 5/0215* (2013.01); *A61B 5/08* (2013.01); *A61B 5/14551* (2013.01)

(58) Field of Classification Search
CPC .. G06F 19/322; G06F 19/328; G06F 19/3456; G06F 19/321; G06F 19/327; G06F 19/345; G06F 19/3487; G06F 19/363; G06F 19/3418; G06F 19/324; G06F 19/3443; G06F 19/366; G06F 19/32; G06Q 50/24; G06K 9/42
USPC ................................................. 715/764, 770
See application file for complete search history.

(56) References Cited

U.S. PATENT DOCUMENTS

| | | |
|---|---|---|
| 5,400,793 A | 3/1995 | Wesseling |
| 5,865,758 A | 2/1999 | Louzianne |
| 6,186,956 B1 | 2/2001 | McNamee |
| 6,348,038 B1 | 2/2002 | Band et al. |

(Continued)

*Primary Examiner* — Sang H Kim

(57) ABSTRACT

A system determines measured patient values for use in clinical calculations using an electronic form including, a first area including data fields for presenting values of the parameters associated with a first part of a cardiac catheterization study of a patient and a second area including data fields for presenting values of the parameters associated with a different second part of a cardiac catheterization study of the patient. A user interface enables a user to copy at least one of the parameters comprising a measured value from the first area to the second area as a substitute value eliminating a need for a re-measurement of the value. A calculation processor automatically calculates a cardiac flow value for incorporation in the second area in response to the measured value being copied into the second area.

18 Claims, 11 Drawing Sheets

(56) References Cited

U.S. PATENT DOCUMENTS

| | | | |
|---|---|---|---|
| 6,463,320 B1 * | 10/2002 | Xue | A61B 5/00 600/523 |
| 6,758,822 B2 | 7/2004 | Romano | |
| 7,024,244 B2 | 4/2006 | Muhlenberg et al. | |
| 7,220,230 B2 | 5/2007 | Roteliuk | |
| 7,251,524 B1 | 7/2007 | Hepp et al. | |
| 7,452,333 B2 | 11/2008 | Roteliuk | |
| 7,666,144 B2 | 2/2010 | Cohen et al. | |
| 7,704,209 B2 | 4/2010 | Bennett et al. | |
| 7,899,683 B2 * | 3/2011 | Schoenberg | G06F 19/322 600/300 |
| 2002/0091728 A1 * | 7/2002 | Kjaer et al. | 707/503 |
| 2004/0032426 A1 * | 2/2004 | Rutledge et al. | 345/764 |
| 2006/0034538 A1 * | 2/2006 | Potter | A61B 5/1075 382/256 |
| 2006/0287600 A1 * | 12/2006 | McEowen | 600/481 |
| 2007/0149884 A1 | 6/2007 | Roteliuk et al. | |
| 2008/0208618 A1 * | 8/2008 | Schoenberg et al. | 705/2 |
| 2009/0019351 A1 * | 1/2009 | Hitchcock et al. | 715/222 |
| 2009/0062666 A1 | 3/2009 | Roteliuk | |
| 2009/0106047 A1 * | 4/2009 | Bay | G06F 19/3487 705/2 |
| 2009/0287095 A1 | 11/2009 | Wassertheurer et al. | |
| 2009/0327888 A1 * | 12/2009 | Woolf et al. | 715/704 |
| 2010/0016735 A1 | 1/2010 | Harpas et al. | |
| 2010/0069761 A1 | 3/2010 | Karst et al. | |
| 2010/0099993 A1 | 4/2010 | Cohen et al. | |
| 2011/0077541 A1 * | 3/2011 | Dong | A61B 5/04525 600/515 |

* cited by examiner

| Actions (workflow steps) [603] | Recording System [605] | Hemo. Worksheet [607] |
|---|---|---|
| The physician inserts a Swan-Ganz (right heart) catheter, connects to a transducer and establishes a pressure waveform signal. | The recording system displays this pressure signal. | N/A |
| The operator measures the patient's IVC pressure and accepts this pressure measurement. | The recording system measures this pressure. | The Hemo WS is populated by this IVC pressure measurement result. |
| The operator clicks on the IVC pressure measurement (hyperlink) from the Hemo WS. | The recording system launches the associated pressure measurement event. | The Hemo WS stays open. (The dialog is modeless). |
| The operator edits the IVC pressure measurement event while viewing the associated waveform. | The recording system accepts the user-edited result for this pressure measurement event. | The Hemo WS dynamically updates the associated pressure measurement result and displays this updated result to the user. |
| The operator measures the patient's IVC O2 saturation and enters this information into a patient monitoring system. | The recording system documents this oxygen saturation and populates the hemodynamic worksheet with this oxygen saturation measurement. | The Hemo WS is populated by the oxygen saturation measurement result. |
| The operator measures the patient's IVC pressure (again) and accepts this pressure measurement. | The recording system measures this pressure without over-writing the existing IVC pressure measurement result. | The Hemo WS is populated by this IVC pressure measurement result. |
| N/A | N/A | The system provides a visual indication that one of these IVC pressure measurements was measured first and the other was measured second. e.g., "IVC1" & "IVC2" |
| The operator measures the patient's RA pressure and accepts this pressure measurement. | The recording system measures this pressure. | The Hemo WS is populated by the RA pressure measurement result. |

Figure 6B

| Actions (workflow steps) 603 | Recording System 605 | Hemo. Worksheet 607 |
|---|---|---|
| The operator measures the patient's RA O2 saturation. | The recording system documents this oxygen saturation and populates the hemodynamic worksheet with this oxygen saturation measurement. | The Hemo WS is populated by the oxygen saturation measurement result. |
| The operator measures the patient's RA to RV push-through pressures and accepts these results. | The recording system measures these pressures (and associated gradient) and populates the hemodynamic worksheet with these pressure measurement results. | The system measures the component pressures (without over-writing the existing RA pressure) and associated gradient; Note: The system does not calculate a valve area as there is not yet one available. |
| The operator measures the patient's RV pressure and accepts this result. | The recording system measures this pressure. | The Hemo WS is populated by this RV pressure measurement result. |
| The operator measures the patient's RV O2 saturation. | The recording system documents this oxygen saturation and populates the hemodynamic worksheet with this oxygen saturation measurement. | The Hemo WS is populated by the oxygen saturation measurement result. |
| The operator measures the patient's RV to PA push-through pressures. | The recording system measures these pressures (and associated gradient) and populates the hemodynamic worksheet with these pressure measurement results. | The system measures the component pressures (without over-writing the existing RV pressure) and associated gradient. |
| The operator measures the patient's PA pressure. | The recording system measures this pressure. | The Hemo WS is populated by this PA pressure measurement result. |
| The operator measures the patient's PA O2 saturation. | The recording system documents this oxygen saturation and populates the hemodynamic | The Hemo WS is populated by the oxygen saturation measurement result. |

Figure 6C

| Actions (workflow steps) | Recording System | Hemo. Worksheet |
|---|---|---|
| The operator measures the patient's PCW pressure. | The recording system measures this pressure. | The Hemo WS is populated by this PCW pressure measurement result. |
| The operator measures the patient's Thermal dilution cardiac output (TDCO) | The recording system documents this TDCO measurement and populates the hemodynamic worksheet with this TDCO measurement.<br><br>The recording system calculates and displays the patient's associated derived calculations (based upon the TDCO) on the hemodynamic worksheet. | The Hemo WS displays the TDCO value (and related values such as SV, SVi, .) and the TV and PA valve area measurements as well as the PAR, PARi, TPR, TPRi measurements.<br><br>Note: The resistance measurements will only be displayed in HRU or ARU units as determined by user configuration. |
| The operator enters the following values into the Fick CO dialog: Patient's VO2, HR and Hb (along with previously entered venous O2 sat.) | The recording system documents these Fick CO entries into the Fick CO dialog and oximetry dialog. | N/A |
| The operator inserts an arterial sheath and pigtail catheter, connects to a transducer and establishes a pressure waveform signal. | N/A | N/A |
| The operator measures the patient's ART pressure and accepts this pressure measurement. | The recording system measures this pressure. | The Hemo WS is populated by this ART pressure measurement result. |
| The operator measures the patient's ART O2 saturation. | The recording system documents this oxygen saturation and populates the hemodynamic worksheet with this oxygen saturation measurement. | The Hemo WS is populated by the oxygen saturation measurement result. |
| The operator enters the following values into the Fick CO dialog: Patient's VO2, HR and Hb (along with previously entered venous O2 sat.) | The recording system documents this Fick CO measurement and populates the hemodynamic worksheet with this TDCO measurement. | The Hemo WS displays the TDCO value (and related values such as SV, SVi, .) and the TV and PA valve area measurements as well as the SVR, SVRi, TSR and TSRi measurements. |

Figure 6D

| Actions (workflow steps) | Recording System | Hemo. Worksheet |
|---|---|---|
| The user selects a new condition. | The system creates a new condition. | The Hemo WS displays the new condition heading and displays any subsequent measured values into this condition (until a new condition is selected by the user.) |
| The operator measures the patient's aortic pressure. | The recording system measures this pressure. | The Hemo WS is populated by the pressure measurement result (into the new condition). |
| The operator measures the patient's ventricular pressure. | The recording system measures this pressure. | The Hemo WS is populated by the pressure measurement result. |
| The operator measures the patient's LV to AO pullback pressures. | The recording system measures these pressures (and associated gradient) and populates the hemodynamic worksheet with this pressure measurement result. | The system measures the component pressures and associated gradient and calculates the aortic valve areas using both the Fick CO and TDCO methods. |
| The operator measures the patient's thermal dilution cardiac output (TDCO) | The recording system documents this TDCO measurement and populates the hemodynamic worksheet with this TDCO measurement. | The Hemo WS replaces the existing valve area and TSR calculations (within this current condition) to now be based upon this new cardiac output measurement. |
| The operator measures the patient's ending aortic pressure. | The recording system measures this pressure. | The Hemo WS is populated by the pressure measurement result. |
| The operator creates a manual RA pressure measurement. | The recording system documents this pressure complete with an asterisk annotation depicting this as a "manually entered pressure." | The Hemo WS displays the patient's calculated SVR value (based upon this user's manually entered RA pressure value.) |
| The user selects a new condition. | The system creates a new condition. | The Hemo WS displays the new condition heading and displays any subsequent values (until a |

WORKSHEET SYSTEM FOR DETERMINING MEASURED PATIENT VALUES FOR USE IN CLINICAL ASSESSMENT AND CALCULATIONS

This is a non-provisional application of provisional application Ser. No. 61/380,757 filed Sep. 8, 2010, by H. Zhang.

FIELD OF THE INVENTION

This invention concerns a system for determining measured patient values for use in clinical calculations by automatically calculating a cardiac flow value for incorporation in an area of a form in response to a measured value being copied between form areas associated with different parts of a cardiac catheterization study of a patient, for example.

BACKGROUND OF THE INVENTION

During a typical cardiac catheterization case, physicians measure many hemodynamic parameters including cardiac flows, pressures (vascular, cardiac chamber, surgical conduit). These parameters provide clinical information and also serve as inputs for various calculations. Physicians also perform these calculations under different conditions separated in time based on clinical status or perhaps following a medication change. Physicians need to be able to view baseline (normal) hemodynamic parameters and also view how these parameters are affected by changes or by spontaneous events (such as an ECG rhythm change). Therefore, sets of parameters are grouped into "conditions". A physician may desire to "re-use" certain parameters by copying these parameters across conditions. An example of this would be "re-using" the cardiac output from a "baseline" condition for use in a "post 100% oxygen administration" condition in order to calculate a valve area in this later condition assuming that the cardiac output stays relatively consistent throughout the time period concerned.

A user needs to be able to quickly and easily understand and troubleshoot clinical information, calculation formulae and computation constants used in calculations. Known systems typically display one pressure measurement per anatomical site, per condition. If more than one pressure measurement per anatomical site, per condition is measured, the system replaces the previous measurement with a new measurement for display and for use in calculations. Therefore, users often switch to a different condition so they can mitigate this limitation. Unfortunately, conditions are created not for the primary reason of segregating clinical states, but instead so that multiple same-site pressures can be measured and documented. As a typical example, a user obtains a patient aortic "baseline" pressure. A user measures patient LV-AO (left ventricular and ascending aortic) pullback pressures and an AO portion of the LV-AO pullback pressure overwrites an initial baseline AO pressure. At the end of the case, the user measures a patient ending AO pressure. So the user uses three different conditions (corresponding to baseline, intermediate and ending pressures) to make sure AO pressures are not over-written.

Known patient monitoring and analysis systems typically do not allow a user to select which input parameter is used in performing particular clinical calculations. If a patient aortic mean pressure is used in calculating a derived calculation of systemic vascular resistance and there are multiple aortic pressures, known systems need to provide the user with some method to select which aortic pressure to use in the calculation (now that there are multiple measurements possible). In known patient monitoring systems, the parameters exist as primary measurements such as pressures and oximetric measurements. Calculations (of resistances, shunt flows, stroke work, valve areas), use the primary measurements as inputs in order to perform calculations. Further, the calculations also often require other inputs such as patient height, weight, heart rate, and constants. Furthermore, a vascular system comprises two circuits in series therefore many of the derived calculations use parameters that measure the flows, resistances and pressures of these circuits much as Ohm's Law parameters are measured within an electrical circuit. In addition, structures of the heart such as walls are assessed by measuring the ventricular pressures, flows, ventricular stroke work and ventricular stroke power.

The heart valves are assessed visually and by valve area measurements for stenosis. The valves can also have incompetence and stenosis concurrently. The heart is also assessed for various types of uncompensated and compensated left, right or combination heart failure as well as systolic and diastolic heart failure. Occasionally, provocative measures are used to examine the severity of disease. A system according to invention principles addresses these tasks, deficiencies and needs and related problems.

SUMMARY OF THE INVENTION

A system uses an updated hemodynamic worksheet (Hemo-WS) to enable a physician to measure hemodynamic values and "borrow" a "surrogate" actual input parameter, deemed stable and reliable for use as input data to support derived calculations. A system determines measured patient values for use in clinical calculations using an electronic form comprising a single display image including labels for values of parameters including blood pressure, ventricular assessments and cardiac flows and multiple image areas. The multiple image areas include, a first area including data fields for presenting values of the parameters associated with a first part of a cardiac catheterization study of a patient and a second area including data fields for presenting values of the parameters associated with a different second part of a cardiac catheterization study of the patient. A user interface enables a user to copy at least one of the parameters comprising a measured value from the first area to the second area as a substitute value eliminating a need for a re-measurement of the value. A calculation processor automatically calculates a cardiac flow value for incorporation in the second area in response to the measured value being copied into the second area.

BRIEF DESCRIPTION OF THE DRAWING

FIG. 2 shows a hemodynamic worksheet listing multiple items, measurements and calculations that is automatically populated with measured values for calculation and estimation of patient health status, according to invention principles.

FIGS. 6A, 6B, 6C and 6D comprise a table showing steps in a process for Hemodynamic worksheet update and pressure data borrowing for cardiac output calculation, according to invention principles.

DETAILED DESCRIPTION OF THE INVENTION

A system uses an updated hemodynamic worksheet (Hemo-WS) to acquire measured hemodynamic values and automatically "borrow" a "surrogate" actual input parameter, deemed stable and reliable for use as input data to support derived calculations. The system provides automatic and adaptive pressure data selection, computation and evaluation for patient procedures by using an updated hemodynamic worksheet. Additionally, the hemodynamic worksheet is used to create and display results of derived calculations based upon available cardiac output methods and to select from more than one pressure measurement (from the same anatomical site) as an input value for use in derived calculations. The system provides a hemodynamic worksheet enabling manual or automatic selection of clinical parameters, such as blood pressure values for use in calculation. The selection of these blood pressures values in the hemodynamic worksheet may involve data copying, averaging, interpolation and combination. The system determines cardiac output and stroke volume using combined, "borrowed", and "surrogate" data values from blood measurement and other sources.

The worksheet provides a readily accessible view of input data and formulas (used in the calculations) enabling a user to troubleshoot unexpected results by performing a comparison calculation manually, for example. An updated hemodynamic worksheet supports a physician in dictating a report and provides a structured view of patient clinical data to facilitate interpretation of patient clinical findings and an optional section comprising a summary view for a referring physician or presenting a preliminary report. In one embodiment, the system provides a user with a summary listing of measured values arranged into condition-associated columns together with derived calculations and enables a user to manipulate a set of input variables in such a way to extract a desired calculated value and view results over a condition-associated time scale. The system supports copying parameters across conditions for use as inputs for calculations and enables a user to use a substitute of a source parameter whilst distinguishing between an actual source measurement and a "borrowed" measurement. This ensures that a measurement is either an actual measurement or a surrogate measurement (linked to a parent actual measurement) and labeled as an inferior (substitute) measurement and labeled with the source of the parent measurement. In addition, same anatomical site source measurements take precedence over substitute measurements.

Figure 1:
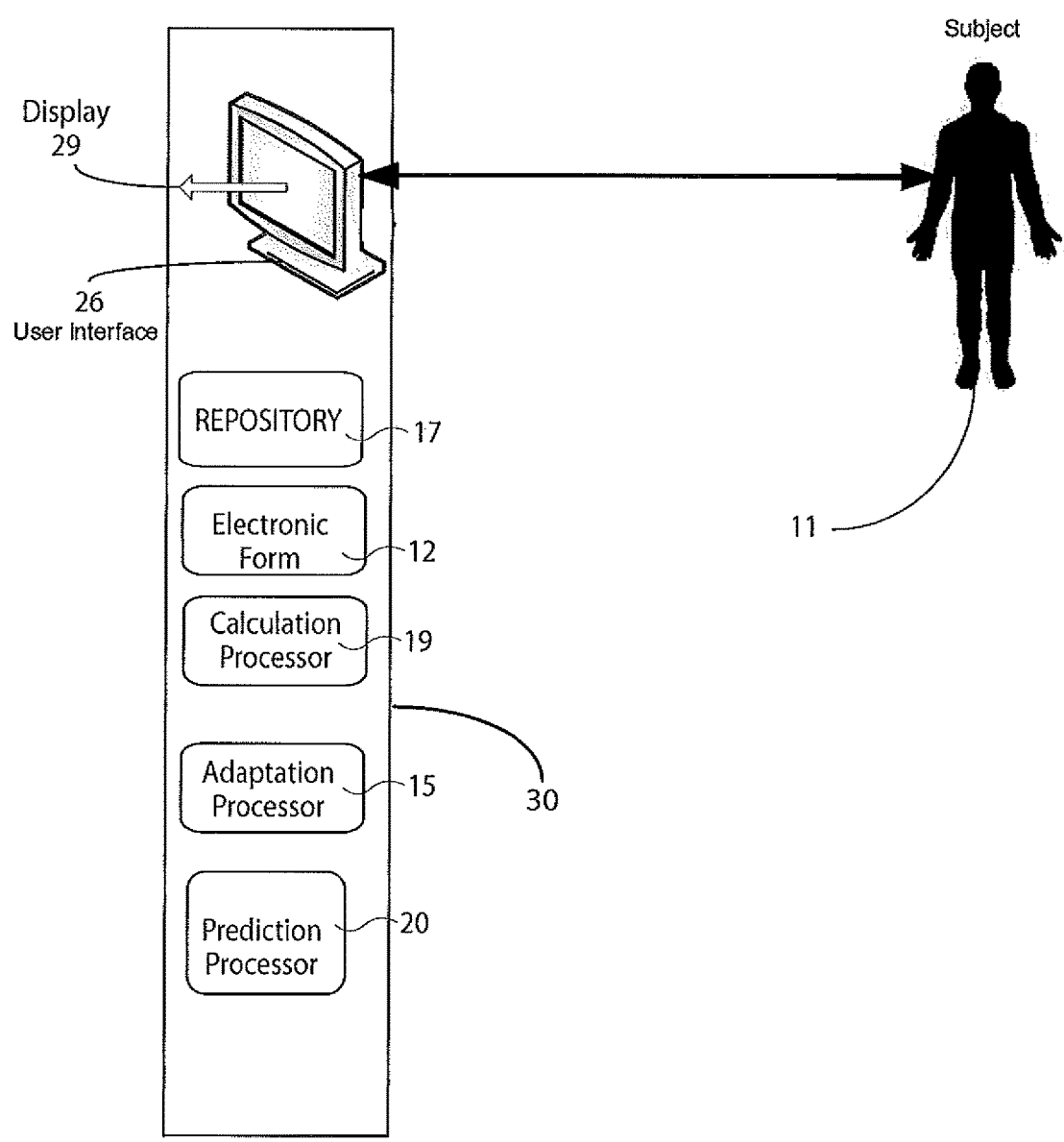
FIG. 1 shows a system for determining measured patient values for use in clinical calculations, according to invention principles.

FIG. 1 shows system 10 for determining measured patient values for use in clinical calculations. System 10 comprises a hemodynamic worksheet and data processing system for use in patient monitoring system 30. System 30 acquires patient monitoring signals from patient 11 and comprises one or more processing devices (e.g., workstations or portable devices such as notebooks, Personal Digital Assistants, phones) that individually include at least one repository 17, a user interface control device 26 such as a keyboard, mouse, touchscreen, voice data entry and interpretation device and display 29, electronic form (hemodynamic worksheet) 12 presented on display 29, calculation processor 19, adaptation processor 15 and prediction processor 20.

Electronic form 12 comprises a single display image including labels for values of parameters including blood pressure, ventricular assessments and cardiac flows and multiple image areas. The multiple image areas include, a first area including data fields for presenting values of the parameters associated with a first part of a cardiac catheterization study of a patient and a second area including data fields for presenting values of the parameters associated with a different second part of a cardiac catheterization study of the patient. User interface 26 enables a user to copy at least one of the parameters comprising a measured value from the first area to the second area as a substitute value eliminating a need for a re-measurement of the value. Calculation processor 19 automatically calculates a cardiac flow value for incorporation in the second area in response to the measured value being copied into the second area. Adaptation processor 15 automatically records data identifying a particular parameter copied by a particular user between a particular type of first area and a particular type of second area. Prediction processor 20, in response to user command, automatically copies parameter values from at least one of, the first area and the second area, to a third area.

System 10 calculates cardiac output and stroke volume using electronic form 12 and associated rules for pressure selection. The content (including measured items, calculation items) in form 12 determined automatically or by a user in response to data indicating a clinical application and may comprise items such as hemodynamic pressure, SPO2 (blood oxygen saturation) and respiration data. System 10 adaptively selects rules and criteria used to generate a form 12 in response to data indicating a clinical application, procedure, treatment or medical condition, for example. System 10 determines and incorporates in electronic form 12 content items including, for example, body surface area (square meters) calculated using predetermined patient data, representative pressures (hiding pressure measurements that are not selected e.g. via checkbox) and measurement units for performed calculations. System 10 saves the state of the form (hemodynamic worksheet) 12 after derived calculations are updated due to borrowing or deleting actions and enables a user to initiate reversion to the saved state.

Figure 2:
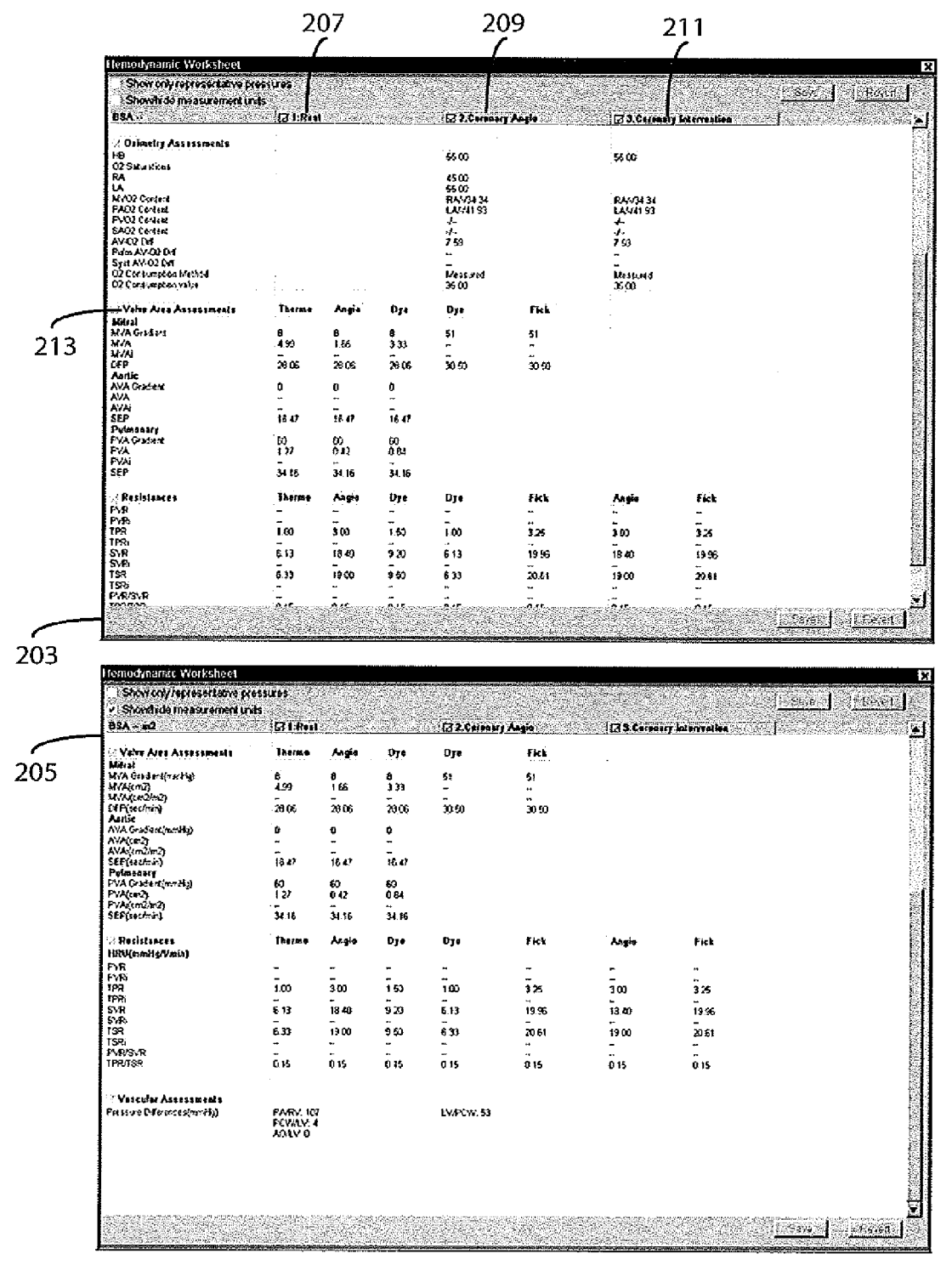

FIG. 2 shows a hemodynamic worksheet form 12 (comprising windows 203, 205) listing multiple items, measurements and calculations that is automatically populated with measured values for calculation, estimation, characterization and monitoring of patient health status. Form 12 presents data for three phases (conditions) of treatment comprising, rest 207 (condition 1), coronary angiography 209 (condition 2) and coronary intervention 211 (condition 3). Form 12 displays data related to particular stages of a procedure or treatment (conditions) in respective columns which demarcate the different parts of a cardiac catheterization study, for example. This study may include different kinds of tests involving exercise or drugs to elicit an accurate understanding of the hemodynamic state of a patient heart. A study may contain multiple conditions which may be hidden or rearranged to facilitate readability and comparability with data from other conditions. Data within a column condition is divided into different sections and collated by row. Sections may be hidden or selected for display via a checkbox. Form 12 shows pressure measurement values (in mmHg) listed in association with a cardiac site label and a measurement timestamp. Further, ventricular assessment data contains pressure measurements that affect the right and left ventricular assessments, such as (dP/dt) Maximum, (dP/dt/P) Maximum, Stroke Work and its index, Stroke Power and its index, and Systolic Ejection Period and Duration and Diastolic Filling Period and Duration for both ventricles.

Form 12 presents cardiac flow values listed by method or type of cardiac output undertaken and include Fick, Thermodynamic, Angiography, or Dye methods. A value acquisition timestamp is associated with the most recently taken cardiac output values, cardiac output index, heart rate, stroke volume, stroke volume index. In case a Fick Shunt is detected, Fick Heart Rate; Pulmonary Blood Flow, $Q_p$, with its own Stroke Volume and Stroke Volume Index; Systemic Blood Flow, $Q_s$, along with its own Stroke Volume and Stroke Volume Index are presented in form 12 by system 10. The direction of the shunt, the Shunt Ratio, Shunt Flow and Shunt Flow Index are also displayed. The Pulmonary to Systemic Blood Flow ratio, $Q_p/Q_s$, is calculated and displayed. If an Angiographic cardiac output determination is performed with another cardiac output method, the regurgitant fraction, along with its stroke work and stroke volume are resented in form 12.

Form 12 further presents oximetry assessments including, Hemoglobin and O2 saturation associated with labels indicating their anatomical measurement site labels. Oxygen contents are presented for Mixed Venous, Pulmonary Artery, Pulmonary Venous, and Systemic Artery vessels. System 10 calculates an arterial venous oxygen difference for presentation as well as Pulmonary and Systemic Arterial and Venous oxygen differences and oxygen consumption method and value. Form 12 provides valve area assessments 213 for each cardiac output method, and including, valve gradients, areas, area indexes, and either systolic or diastolic filling and ejection periods for the different valves, Mitral, Tricuspid, Aortic and Pulmonary. Form 12 also presents resistances in either Woods Units, also called Hybrid Resistance Units (mmHg/L/min), or in Metric Resistance Units (dynes·sec/cm$^5$). These measurements include Pulmonary Vascular Resistance and its index, Total Pulmonary Resistance and its index, Systemic Vascular Resistance and its index, Total Systemic Resistance and its index, Pulmonic and Systemic Vascular Resistance Ratio and Total Pulmonary to Systemic Vascular Ratio, and predicted Pulmonary and Systemic Vascular Resistance values. Also form 12 shows vascular assessments including instantaneous pressure difference values between vascular sites (in mmHg).

Figure 3:
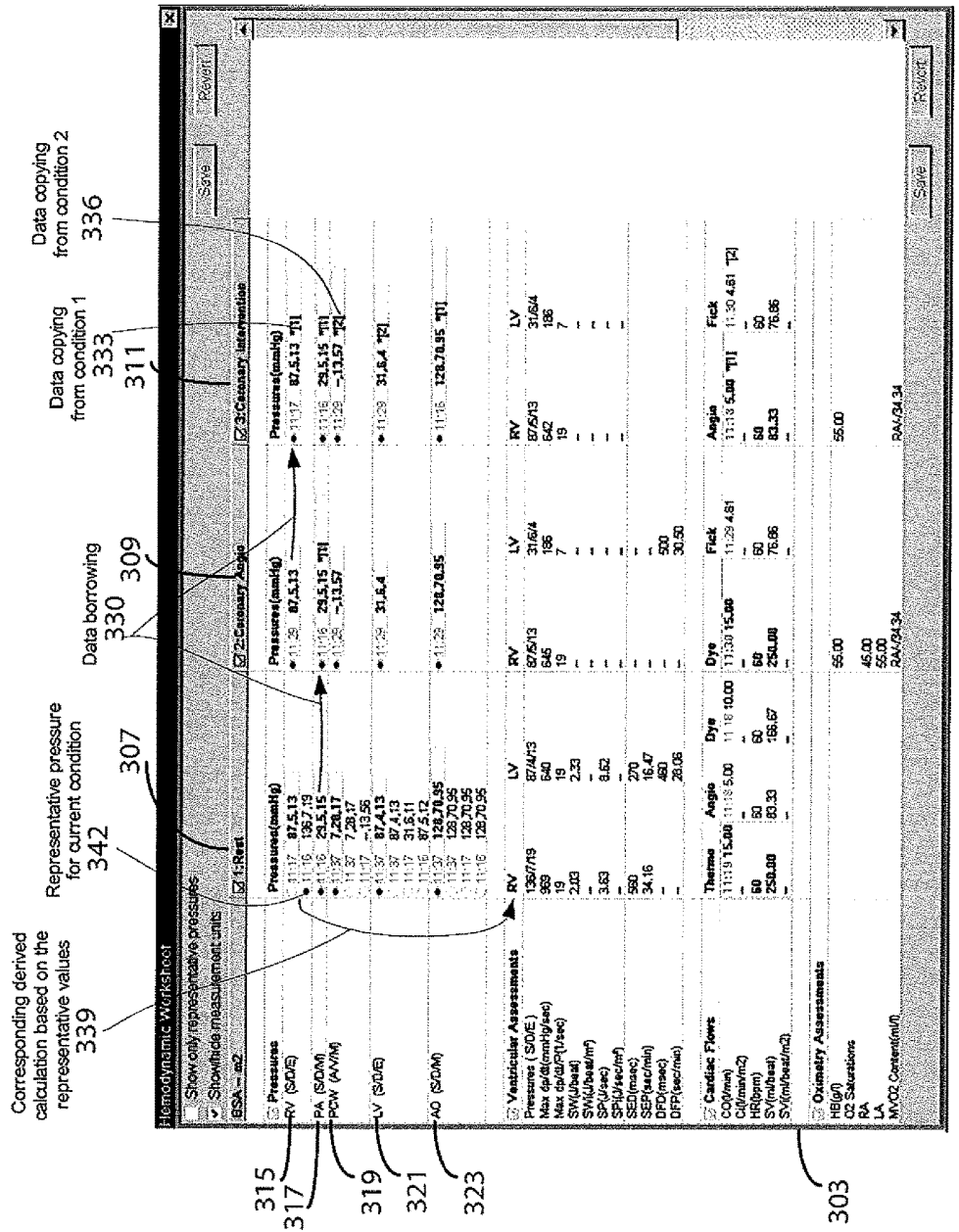
FIG. 3 shows a Hemodynamic worksheet indicating borrowing of values derived in different phases of a procedure, according to invention principles.

FIG. 3 window 303 shows hemodynamic worksheet form 12 indicating borrowing of values derived in different phases of a procedure in response to predetermined rules in repository 17. Borrowing herein is used synonymously with the term copying. Pressure values indicated by black dot are borrowed between rest 307 (condition 1), coronary angiography 309 (condition 2) and coronary intervention 311 (condition 3). Specifically, pressure values for right ventricle (RV) on row 315, pulmonary artery (PA) on row 317, pulmonary capillary wedge (PCW) on row 319, left ventricle (LV) on row 321 and ascending aorta (AO) on row 323 indicated by black dot are borrowed between the conditions. In FIG. 3 indicates a pressure value is borrowed from condition 1, [2] indicates a pressure value is borrowed from condition 2. The arrows in FIG. 3 show pressure values borrowed and value updates. RV pressure values in condition 3 and condition 2 are borrowed (330, 333) from condition 1 and via condition 2. PCW pressure values in condition 3 are borrowed (336) from condition 2. PA pressure values in condition 2 are borrowed (330) from condition 1. A PA pressure value 342 is copied (339) to a ventricular assessment section and used in subsequent calculations.

Figure 4:
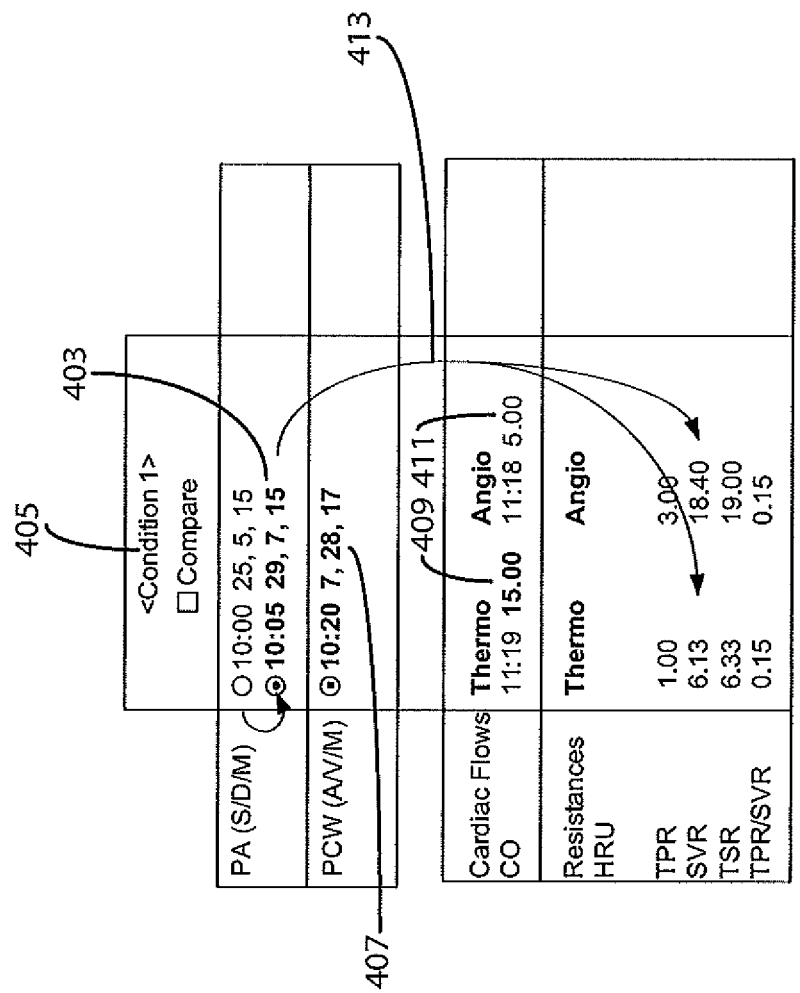
FIG. 4 shows data workflow and calculation actions within one condition in a hemodynamic worksheet, according to invention principles.

FIG. 4 shows data workflow and calculation actions within one condition in hemodynamic worksheet form 12. A pulmonary arterial pressure 403 taken at 10:05 is designated as a representative pressure measurement for Condition 1 (405) through user action. Since the user has also measured a pulmonary capillary wedge pressure 407 and has performed two cardiac outputs 409, 411 using thermodynamic and Angiography methods in this condition, in response to a user changing the representative pulmonary arterial pressure 403, calculation processor 19 (FIG. 1) in the resistances section automatically recalculates and updates each cardiac output value 409, 411 derived by the different methods. Further in response to an updated pulmonary arterial pressure, resistance values are automatically updated 413 by system 10.

Figure 5:
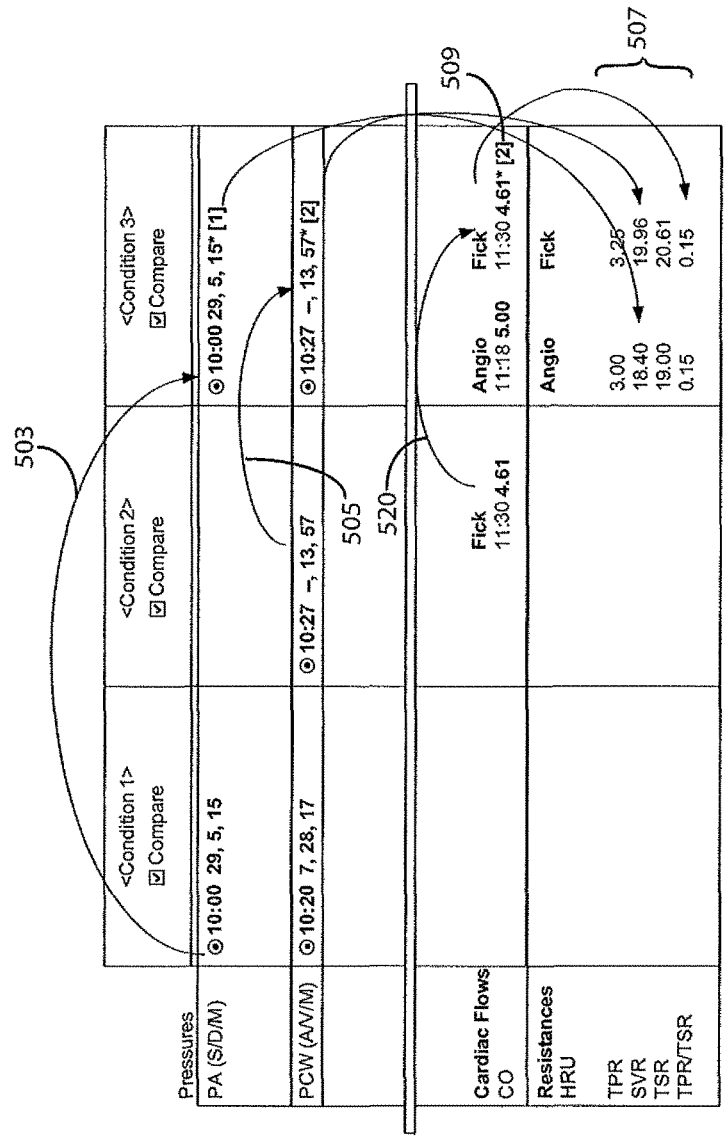
FIG. 5 shows manual data borrowing between different conditions in a hemodynamic worksheet, according to invention principles.

FIG. 5 shows manually performed or automatic data borrowing between different conditions in a hemodynamic worksheet form 12. In simulating hemodynamic data changes, a pulmonary arterial pressure taken at 10:00 is borrowed (503) in response to user action or automatically, from condition 1 to condition 3 where no measurement has been taken. A pulmonary capillary wedge pressure is similarly borrowed (505) from condition 2 to condition 3. Condition 3 shows measurements from condition 1 and 2 that are used for simulation purposes. Since a pulmonary arterial pressure, a pulmonary capillary wedge pressure, and a cardiac output 509 are available in condition 3 through actual and borrowed measurements, resistance values 507 are substantially automatically immediately calculated or updated along with a resistance ratio. Calculation processor 19 (FIG. 1) identifies a resistance calculation input is missing in condition 3 and automatically borrows the most recently acquired necessary values from conditions 1 and 2 to calculate resistances for condition 3. A displayed image distinguishes by visual attribute those values that are borrowed automatically from those values that are borrowed manually. A visual attribute comprises color, highlighting, shading, shape, bolding and dashed lines, for example. Calculation processor 19 in response to detecting an absent calculation value, automatically borrows 503 the pulmonary arterial pressure value from condition 1 and borrows 505 the pulmonary capillary wedge pressure value from condition 2 and borrows 520 a cardiac output pressure from condition 2, and uses the borrowed values in calculating resistance values 507 and a resistance ratio, for example.

A user employs hemodynamic worksheet form 12 to perform clinical related actions, such as data copying, calculations and save and delete functions. Form 12 automatically simulates different hemodynamic effects by calculating cardiac output and other parameters during a cardiac catheterization study, for example. Form 12 enables a user to select pressures and cardiac outputs for simulating hemodynamic effects within different scenarios in different ways. A user uses a tab key or mouse to select a pressure value and designate a pressure value within a condition as being a representative pressure for that condition. This action updates calculations within that condition that may be influenced by the measured pressure value. In the case of cardiac output values, multiple cardiac output values of the same type that are determined within a particular condition are averaged or otherwise used to provide a calculated cardiac output value of a given type within the condition. System 10 enables a cardiac output value to be selected by right-click or drag and drop function, for example, to invoke a contextual menu. The system responds by highlighting the source measurement to indicate that the measurement is ready for a next user action.

A user copies pressures and cardiac outputs between conditions for simulating different scenarios using derived calculations by first selecting a non-borrowed pressure measurement or cardiac output from a source condition. The user copies and pastes a value using a right-mouse-button-click (hereafter, right-click) contextual menu or by using a keystroke combination (such as CTRL or control key+C), to "copy" the measurement, (and CTRL+V, to "paste" the measurement in the target condition, for example), from a source condition to another condition where a pressure measurement or calculated value is absent. In another embodiment a user selects a target condition to invoke a contextual menu, and selects from a list of pressure measurements and cardiac outputs that are eligible for affecting the derived calculations in that particular condition. At the completion of user interaction, calculations affected by a borrowed pressure or cardiac output are updated. Vascular resistance calculations are updated when appropriate pressure measurements and at least one cardiac output value become available. When cardiac output values become available and other pre-requisites are met, valve area calculations are updated, which also triggers ventricular assessment calculations, as well as vascular resistance calculations. In addition, a borrowed pressure measurement or cardiac output value is presented with a visual attribute identifying it is a borrowed measurement by identifying from which source condition it was borrowed e.g., using a condition identifier such as "[1]".

In response to a pressure measurement or cardiac output value derived from measured values being obtained in a target condition, system 10 overwrites a borrowed measurement with the value and unless it is deleted, a pressure measurement or cardiac output is prevented from being copied (borrowed) into this condition. A user may delete borrowed pressure and cardiac output measurements from a condition by selecting them and deleting the borrowed measurement. If a borrowed pressure measurement is designated as being a representative pressure for that condition and it is deleted, the next most recent pressure measurement for that site is designated as being the representative pressure, and so on chronologically, until there are no more borrowed pressure measurements remaining in that section. At the completion of user action, derived calculations affected by a delete action are immediately updated. In response to update of derived calculations dependent on pressures or cardiac outputs, system 10 saves the state of form 12 in memory. In response to a successful save, the system employs a revert function to return the worksheet to the last saved state. In one embodiment, hemodynamic worksheet form 12 employs a borrowed value to calculate a parameter that is used to track variation and variability of parameters of different conditions.

In an embodiment, hemodynamic worksheet form 12 automatically borrows and updates clinical data among different conditions in order to simulate hypothetical hemodynamic effects. In FIG. 5, a resistance calculation is performed by automatically borrowing 503, 505, 520 data items in form 12. System 10 automatically compares data items (measured and calculated using measured and borrowed items) of the different conditions. System 10 automatically simulates hemodynamic effects in a condition where resistance calculation inputs are absent by automatically borrowing most recently acquired values required for a resistance calculation from condition 1 and 2 to calculate resistances in condition 3. System 10 uses a visual attribute to differentiate manually borrowed inputs from automatically borrowed inputs. System 10 automatically calculates resistance values and a resistance ratio and presents the calculated data as a variant simulated scenario. System 10 also predicts hemodynamic values based on previously or currently acquired study data and presents the data in form 12.

FIGS. 6A, 6B, 6C and 6D comprise a table showing steps in a process for hemodynamic worksheet form 12 (FIG. 1) update and pressure data borrowing for cardiac output calculation. Column 603 indicate clinical action (steps) and corresponding workflow for a right and left heart study involving patient data monitoring (recording) system 30 and update of hemodynamic worksheet form 12. In successive rows of columns 605 and 607 indicate actions occurring in the patient data recording system and hemodynamic worksheet form 12 respectively, corresponding to clinical workflow actions indicated in successive rows of column 603. The clinical actions in column 603 are initiated by a physician inserting a Swan-Ganz (right heart) catheter, connecting it to a transducer and establishing a pressure waveform signal. An operator measures a patient IVC (Inferior vena cava) pressure and accepts this pressure measurement. The operator clicks on the IVC pressure measurement (hyperlink) in form 12 and edits the IVC pressure measurement event while viewing the associated waveform. The operator measures the patient IVC O2 saturation and enters this information into a patient monitoring system. The operator measures the patient IVC pressure (again) and accepts this pressure measurement and measures the patient RA pressure and accepts the pressure measurement.

The operator measures the patient RA O2 saturation and RA to RV push-through pressures and accepts these results. The operator also measures the patient RV pressure and accepts this result. The operator measures the patient RV O2 saturation, RV to PA push-through pressures and patient PA pressure and measures the patient PA O2 saturation, PCW pressure and thermal dilution cardiac output (TDCO). The operator enters the values into the Fick CO dialog window including patient VO2, HR and Hb (along with previously entered venous O2 saturation) and inserts an arterial sheath and pigtail catheter, connects a transducer and establishes a pressure waveform signal. The operator measures the patient ART pressure and accepts this pressure measurement, measures the patient ART O2 saturation and enters values into the Fick CO dialog window including Patient VO2, HR and Hb (along with previously entered venous O2 saturation). The user selects a new condition, measures patient aortic pressure, ventricular pressure and LV to AO pullback pressures. The operator further measures the patient thermal dilution cardiac output (TDCO) and ending aortic pressure and creates a manual RA pressure measurement.

Figure 7:
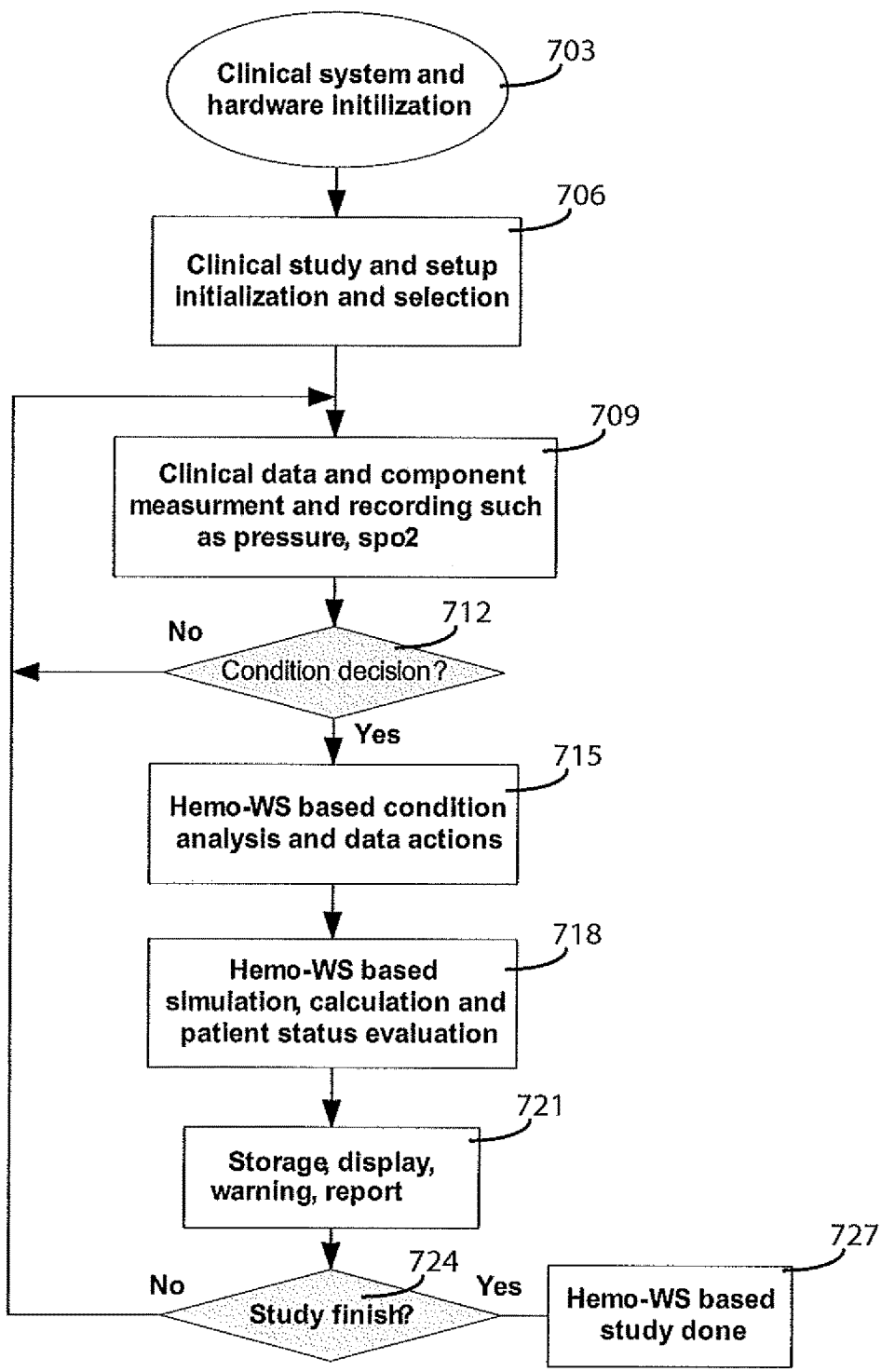
FIG. 7 shows a flowchart of a process using a Hemodynamic worksheet for patient status calculation, estimation and evaluation, according to invention principles.

FIG. 7 shows a flowchart of a process using hemodynamic worksheet form 12 (FIG. 1) for patient status calculation, estimation and evaluation. System 10 is initialized in step 703 and a type of clinical study and setup configuration is selected in step 706. In step 709 clinical data and parameters including pressures, SpO2 (blood oxygen saturation) and other parameters are iteratively measured and recorded in repository 17 by patient monitoring system 30 for different conditions until data for the different conditions has been recorded in form 12 data fields as determined in step 712. The conditions in one embodiment include, rest (condition 1), coronary angiography (condition 2) and coronary intervention (condition 3), for example. In step 715 system 10 processes the data of hemodynamic worksheet form 12 to detect absent items needed for calculation of cardiac output and other parameters for incorporation in form 12 and in step 718, calculation processor 19 calculates cardiac output and other parameters for incorporation in form 12. Calculation processor 19 performs simulation of conditions in response to automatically (or manually) copied pressures and cardiac outputs between conditions for simulating different scenarios using derived calculations. In step 721, calculated parameters are stored and compared with predetermined ranges and thresholds and an alert message is generated for communication to a user or presentation on display 29 in response to a determination a calculated parameter exceeds a threshold. Steps 709-721 are iteratively repeated until it is determined in step 724 that a study is completed whereupon the hemodynamic study is marked complete in step 727.

Figure 8:
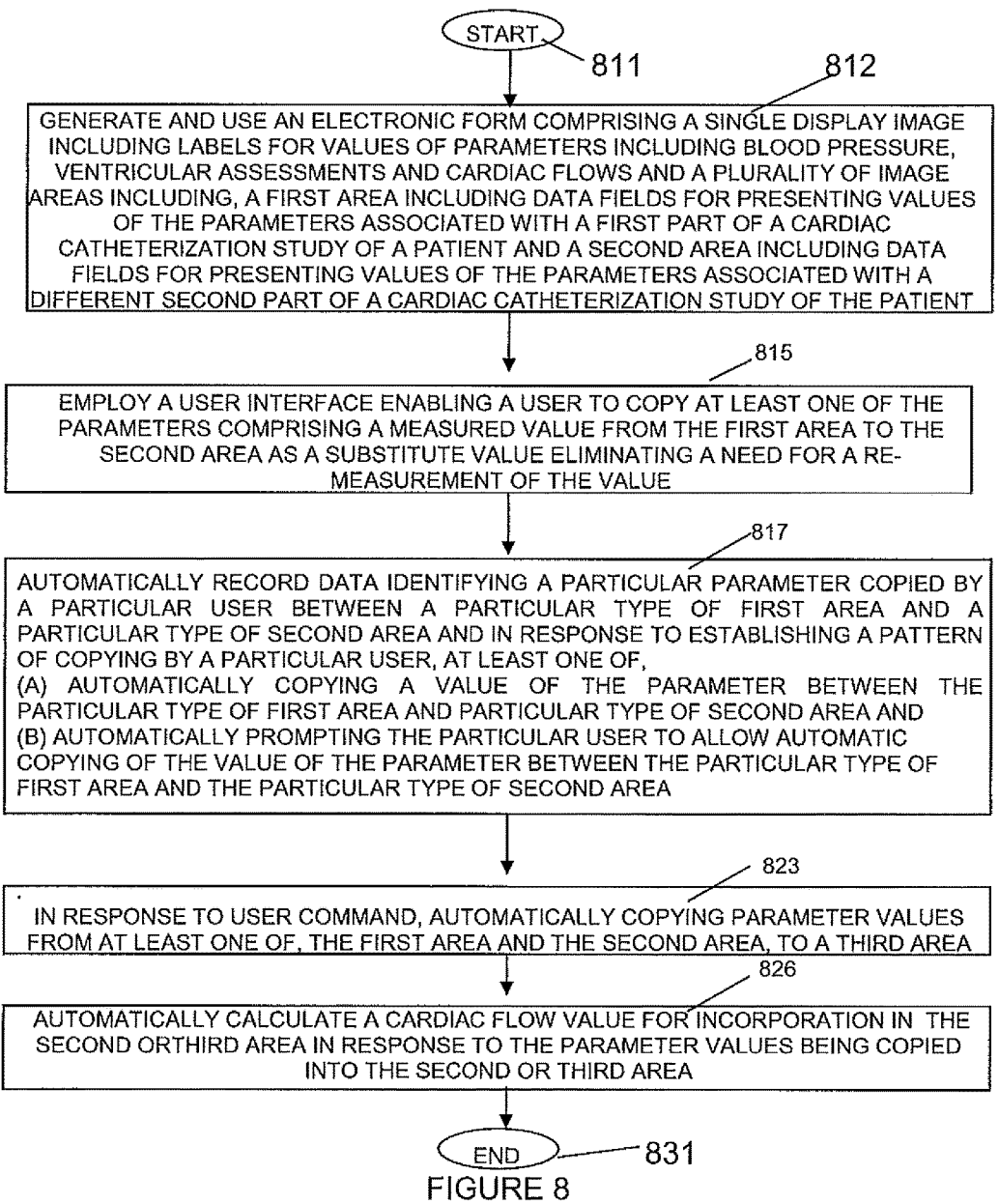
FIG. 8 shows a flowchart of a process used by a system for determining measured patient values for use in clinical calculations, according to invention principles.

FIG. 8 shows a flowchart of a process used by system 10 (FIG. 1) for determining measured patient values for use in clinical calculations. In step 812 following the start at step 811, system 30 generates and uses electronic form 12 comprising a single display image including labels for values of parameters including blood pressure, ventricular assessments, oximetry assessments and cardiac flows and multiple image areas. The multiple image areas include, a first area including data fields for presenting values of the parameters associated with a first part of a cardiac catheterization study of a patient and a second area including data fields for presenting values of the parameters associated with a different second part of a cardiac catheterization study of the patient. The first and second parts of the cardiac catheterization study comprise different portions of a cardiac catheterization study and the first and second areas comprise substantially adjacent first and second rows or groups of rows or columns respectively.

In step 815 user interface 26 enables a user to copy at least one of the parameters comprising a measured value from the first area to the second area as a substitute value eliminating a need for re-measurement of the value. The measured value comprises at least one of, (a) a blood pressure value and (b) a blood oxygen saturation value. User interface 26 initiates storing of data associating the substitute value with the corresponding measured value and with a form 12 data field of the measured value and in response to deletion of the measured value, calculation processor 19 deletes the substitute value and updates cardiac flow calculations using the substitute value. The single display image employs a visual attribute to distinguish between the measured value and the substitute value. Form 12 excludes use of more than one substitute value in the plurality of adjacent areas.

In step 817, adaptation processor 15 automatically records data identifying a particular parameter copied by a particular user between a particular type of first area and a particular type of second area. In response to establishing a pattern of copying by a particular user, processor 15 at least one of, (a) automatically copies a value of the parameter between the particular type of first area and particular type of second area and (b) automatically prompts the particular user to allow automatic copying of the value of the parameter between the particular type of first area and the particular type of second area. Adaptation processor 15 establishes the pattern of copying by the particular user in response to a number of times the particular user copied a value of the parameter between the particular type of first area and particular type of second area. Adaptation processor 15 enables a user to simulate effect of a particular parameter value by entering data in the form representing the particular parameter value and initiating automatic update of cardiac flow values in response to the entered particular parameter value by calculation processor 19.

In step 823 prediction processor 20, in response to user command, automatically copies parameter values from at least one of, the first area and the second area, to a third area. Processor 20 in step 826 calculation processor 19 automatically calculates a cardiac flow value for incorporation in the second or third area in response to the parameter values being copied into the second or third area. Calculation processor 19 automatically calculates a cardiac flow value by giving higher precedence to a measured value than a corresponding substitute value. The cardiac flow value comprises at least one of, (a) a stroke value and (b) a cardiac output value. The process of FIG. 8 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system uses an updated hemodynamic worksheet to acquire measured hemodynamic values and automatically copies measured values between different portions of a study, for example, to calculate values and selects from more than one pressure measurement (from the same anatomical site) as an input value for use in derived calculations. Further, the processes and applications may, in alternative embodiments, be located on one or more (e.g., distributed) processing devices on a network linking the units of FIG. 1. Any of the functions and steps provided in FIGS. 1-8 may be implemented in hardware, software or a combination of both.

What is claimed is:

1. A system for determining measured patient values for use in clinical calculations, comprising:
    a repository operative to record values of parameters;
    an electronic form comprising a single display image including labels for values of parameters including blood pressure, ventricular assessments and cardiac flows and a plurality of image areas including,
        a first area of the single display image including data fields for presenting values of said parameters associated with a first part of a cardiac catheterization study of a patient; and
        a second area of the single display image including data fields for presenting values of said parameters associated with a different second part of a cardiac catheterization study of said patient, wherein the values presented in the first area of the single display image and the values presented in the second area are associated with the same parameters and at least one value presented in the first area and associated with a first parameter is different from a value presented in the second area and associated with the first parameter;
    a user interface enabling a user to copy a second measured value presented in the first area and associated with a second parameter to said second area of the single display image as associated with the second parameter in the second part of the cardiac catheterization study, said user interface displaying a visual attribute in said second area to indicate that the second measured value in the second area is a substitute value which was measured in the first part of the cardiac catheterization study and was not measured in the second part of the cardiac catheterization study and has been copied to said second area from said first area, the second measured value to be used as an input in calculations instead of newly measured data; and
    a calculation processor for automatically calculating a cardiac flow value for the second part of the cardiac catheterization study using the second measured value in response to said second measured value being copied to said second area, and automatically simulating hemodynamic effects in a condition based on the copied second measured value, wherein the calculation processor includes a non-transitory memory operative to store instructions regarding the automatic calculation of the cardiac flow value.

2. The system according to claim 1, wherein said parameters include oximetry assessments.

3. The system according to claim 1, wherein said cardiac flow value comprises at least one of (a) a stroke value and (b) a cardiac output value.

4. The system according to claim 1, wherein the first and second parts of the cardiac catheterization study comprise different portions of a cardiac catheterization study.

5. The system according to claim 1, wherein the first and second areas comprise substantially adjacent first and second columns respectively.

6. The system according to claim 1, wherein the first and second areas comprise substantially adjacent first and second rows or groups of rows respectively.

7. The system according to claim 1, including an adaptation processor for automatically recording data identifying a particular parameter copied by a particular user between a particular type of first area and a particular type of second area and in response to establishing a pattern of copying by a particular user, at least one of,
    (a) automatically copying a value of the parameter between the particular type of first area and particular type of second area and
    (b) automatically prompting the particular user to allow automatic copying of the value of the parameter between the particular type of first area and the particular type of second area.

8. The system according to claim 7, wherein said adaptation processor establishes said pattern of copying by said particular user in response to a number of times said particular user copied a value of the parameter between the particular type of first area and particular type of second area.

9. The system according to claim 1, including a prediction processor for, in response to user command, automatically copying parameter values from at least one of; said first area and said second area, to a third area and
said calculation processor automatically calculates a cardiac flow value for incorporation in said third area in response to said parameter values being copied into said third area.

10. The system according to claim 1, wherein said measured value comprises at least one of, (a) a blood pressure value and (b) a blood oxygen saturation value.

11. The system according to claim 1, wherein said user interface initiates storing of data associating said substitute value with the corresponding measured value and with a form data field of the measured value and in response to deletion of said measured value, said calculation processor deletes said substitute value and updating cardiac flow calculations using the substitute value.

12. The system according to claim 1, including
an adaptation processor enabling a user to simulate effect of a particular parameter value by entering data in said form representing said particular parameter value and initiating automatic update of cardiac flow values in response to the entered particular parameter value by said calculation processor.

13. The system according to claim 1, wherein
said calculation processor automatically calculates a cardiac flow value by giving higher precedence to a measured value than a corresponding substitute value.

14. The system according to claim 1, wherein
said form excludes use of more than one substitute value in said plurality of adjacent areas.

15. A method for determining measured patient values for use in clinical calculations, comprising the activities of:
using an electronic form comprising a single display image including labels for values of parameters including blood pressure, ventricular assessments and cardiac flows and a plurality of image areas including,
a first area of the single display image including data fields for presenting values
of said parameters associated with a first part of a cardiac catheterization study of a patient; and
a second area of the single display image including data fields for presenting
values of said parameters associated with a different second part of a cardiac catheterization study of said patient, wherein the values presented in the first area of the single display image and the values presented in the second area are associated with the same parameters and at least one value presented in the first area and associated with a first parameter is different from a value presented in the second area and associated with the first parameter;
enabling a user to copy a second measured value presented in the first area and associated with a second parameter to said second area of the single display image as associated with the second parameter in the second part of the cardiac catheterization study, said copying resulting in display of a visual attribute in said second area to indicate that the second measured value in the second area is a substitute value which was measured in the first part of the cardiac catheterization study and was not measured in the second part of the cardiac catheterization study and has been copied to said second area from said first area, the second measured value to be used as an input in calculations instead of newly measured data; and
automatically calculating a cardiac flow value and automatically simulating hemodynamic effects for the second part of the cardiac catheterization study using the second measured value in response to said second measured value being copied to said second area.

16. A method for determining measured patient values for use in clinical calculations, comprising:
using an electronic form comprising a single display image including labels for values of parameters including blood pressure, ventricular assessments and cardiac flows and a plurality of image areas including,
a first area of the single display image including data fields for presenting values
of said parameters associated with a first part of a cardiac catheterization study of a patient; and
a second area of the single display image including data fields for presenting
values of said parameters associated with a different second part of a cardiac catheterization study of said patient, wherein the values presented in the first area of the single display image and the values presented in the second area are associated with the same parameters and at least one value presented in the first area and associated with a first parameter is different from a value presented in the second area and associated with the first parameter;
detecting in the second area a missing value of a second parameter, wherein the missing value is a variable of an equation associated with the second area;
copying a measured value of the second parameter from the first area of the single display image to the second area of the single display image to be associated with the second parameter in the second area;
displaying a visual attribute in said second area to indicate that the second measured value associated with the second parameter in the second area is a substitute value which was measured in the first part of the cardiac catheterization study and was not measured in the second part of the cardiac catheterization study and has been copied to said second area from said first area, the second measured value to be used as an input in calculations, and for automatic simulation of hemodynamic effects in a condition, instead of newly measured data;
automatically recording data identifying a particular parameter copied by a particular user between a particular type of first area and a particular type of second area and, in response to determining a pattern of copying by a particular user, at least one of
(a) automatically copying a value of the particular parameter between the particular type of first area and particular type of second area and
(b) automatically prompting the particular user to allow automatic copying of the value of the particular parameter between the particular type of first area and the particular type of second area.

17. A system for determining measured patient values for use in clinical calculations, comprising:
a repository operative to record values of parameters;
an electronic form comprising a single display image including labels for values of parameters including blood pressure, ventricular assessments and cardiac flows and a plurality of image areas including,
a first area of the single display image including data fields for presenting values
of said parameters associated with a first part of a cardiac catheterization study of a patient; and
a second area of the single display image including data fields for presenting
values of said parameters associated with a different second part of a cardiac catheterization study of said patient, wherein the values presented in the first area of the single display image and the values presented in the second area are associated with the same parameters and at least one value presented in the first area and associated with a first parameter is different from a value presented in the second area and associated with the first parameter;
a prediction processor for, in response to user command, automatically copying parameter values from at least one of said first area and said second area to a third area of the single display image, wherein prior to copying, it is determined that the parameter values are missing from the third area and the missing parameter values are variables of an equation associated with the third area of the single display image, wherein the prediction processor includes a non-transitory memory operative to store instructions regarding the automatic copying of parameter values, said copying resulting in display of one or more visual attributes in said third area to indicate that the parameter values copied to the third area are substitute values which were measured in the cardiac catheterization study and were not in the third area prior to copying and have been copied to said third area from said first area or from said second area, the parameter values copied to the third area are to be used as an input in calculations instead of newly measured data; and a calculation processor for automatically calculating a cardiac flow value associated with said third area of the single display image using the parameter values copied to the third area in response to said parameter values being copied into said third area, and automatically simulating hemodynamic effects in a condition based on the copied parameter values to the third area, wherein the calculation processor includes a non-transitory memory operative to store instructions regarding the automatic calculation of the cardiac flow value.

18. The system according to claim 17, including a user interface enabling a user to copy a second value presented in the first area and associated with a second parameter to said second area as associated with the second parameter.

* * * * *